(12) United States Patent
Patel et al.

(10) Patent No.: US 10,299,530 B2
(45) Date of Patent: May 28, 2019

(54) HEADGEAR FOR PROTECTIVE HEADWEAR

(71) Applicant: ILLINOIS TOOL WORKS, INC., Glenview, IL (US)

(72) Inventors: Nishank R. Patel, Appleton, WI (US); Eric T. Sommers, Appleton, WI (US); Mark D. Begin, Madison, WI (US); Samuel B. Petre, Wauwatosa, WI (US)

(73) Assignee: ILLINOIS TOOL WORKS INC., Glenview, IL (US)

( * ) Notice: Subject to any disclaimer, the term of this patent is extended or adjusted under 35 U.S.C. 154(b) by 0 days.

(21) Appl. No.: 14/722,664

(22) Filed: May 27, 2015

(65) Prior Publication Data

US 2015/0359676 A1    Dec. 17, 2015

Related U.S. Application Data

(60) Provisional application No. 62/012,483, filed on Jun. 16, 2014.

(51) Int. Cl.
*A61F 9/06* (2006.01)
*A42B 3/08* (2006.01)
(Continued)

(52) U.S. Cl.
CPC ............... *A42B 3/085* (2013.01); *A42B 3/14* (2013.01); *A42B 3/145* (2013.01); *A42B 3/225* (2013.01); *A61F 9/06* (2013.01)

(58) Field of Classification Search
CPC ........... A42B 3/14; A42B 3/085; A42B 3/145; A42B 3/225; A61F 9/06; A61F 9/025
(Continued)

(56) References Cited

U.S. PATENT DOCUMENTS

| 1,182,367 A | 5/1916 | Gravell |
| 1,338,022 A | 4/1920 | Lamoreaux |

(Continued)

FOREIGN PATENT DOCUMENTS

| CN | 101056677 A | 10/2007 |
| CN | 101795645 A | 8/2010 |

(Continued)

OTHER PUBLICATIONS

International Search Report and Written Opinion for PCT/US2015/033054 dated Aug. 31, 2015, 12 pages.

(Continued)

*Primary Examiner* — Richale L Quinn
*Assistant Examiner* — Anne M Kozak
(74) *Attorney, Agent, or Firm* — Klintworth & Rozenblat IP LLP

(57) ABSTRACT

In one aspect, a headgear for engaging and supporting protective headwear on a wearer's head is provided. The headgear may include a first side member on a first side of the headgear, a second side member on a second side of the headgear, and a forehead strap pivotally coupled to and extending between the first and second side members. The forehead strap may be configured to engage a wearer's forehead with the headgear worn by a wearer. The headgear may also include a second strap coupled to and extending between the first and second side members.

19 Claims, 9 Drawing Sheets

(51) Int. Cl.
*A42B 3/14* (2006.01)
*A42B 3/22* (2006.01)

(58) Field of Classification Search
USPC .................................................. 2/8.2
See application file for complete search history.

(56) References Cited

U.S. PATENT DOCUMENTS

| | | | |
|---|---|---|---|
| 1,601,830 A * | 10/1926 | Huntsman | A61F 9/06 2/8.2 |
| 1,994,103 A | 3/1935 | Huey | |
| 2,169,745 A * | 8/1939 | Shipman | A61F 9/02 2/8.2 |
| 2,194,492 A | 3/1940 | Bowers | |
| 2,402,820 A | 6/1946 | Kitchen | |
| 2,411,831 A | 11/1946 | Lehmberg et al. | |
| 2,487,848 A * | 11/1949 | Bowers | A61F 9/06 2/8.1 |
| 2,658,200 A * | 11/1953 | Bowers, Sr. | A61F 9/06 2/8.1 |
| 2,700,158 A * | 1/1955 | Larsen | A61F 9/06 2/453 |
| 2,763,006 A * | 9/1956 | Amundsen | A61F 9/025 2/8.1 |
| 3,074,072 A | 1/1963 | Edwards et al. | |
| 3,112,745 A | 12/1963 | Boyer | |
| 3,119,279 A | 1/1964 | Reece | |
| 3,214,768 A | 11/1965 | Bohner | |
| 3,413,972 A | 12/1968 | Depping | |
| 3,430,263 A | 3/1969 | Newcomb | |
| 3,584,314 A | 6/1971 | Hobson | |
| 3,609,765 A | 10/1971 | Molitoris | |
| 3,696,442 A * | 10/1972 | Amundsen | A61F 9/06 2/8.1 |
| 3,868,727 A | 3/1975 | Paschall | |
| 3,881,478 A | 5/1975 | Rosendahl | |
| 3,914,796 A | 10/1975 | Barta | |
| 3,955,570 A | 5/1976 | Hutter, III | |
| 4,011,865 A | 3/1977 | Morishita | |
| 4,040,123 A | 8/1977 | Williams | |
| 4,080,664 A | 3/1978 | Morris et al. | |
| 4,109,320 A | 8/1978 | Anderson | |
| 4,293,757 A | 10/1981 | Niemi | |
| 4,335,472 A | 6/1982 | Rappleyea | |
| D270,642 S | 9/1983 | Watts | |
| 4,464,800 A | 8/1984 | Edwards | |
| 4,479,738 A | 10/1984 | Kubnick | |
| 4,499,630 A | 2/1985 | Harris | |
| 4,793,001 A | 12/1988 | Accardi | |
| 4,853,973 A | 8/1989 | Boochard | |
| D316,020 S | 4/1991 | Fushiya | |
| 5,003,632 A | 4/1991 | Claude | |
| 5,012,528 A | 5/1991 | Pernicka | |
| 5,040,528 A | 8/1991 | O'Neill | |
| 5,044,019 A | 9/1991 | Shewchenko | |
| 5,077,836 A | 1/1992 | Idoff et al. | |
| D329,590 S | 9/1992 | Chapman | |
| 5,386,592 A | 2/1995 | Checkeroski | |
| 5,412,811 A * | 5/1995 | Hildenbrand | A42B 3/0433 2/10 |
| D365,666 S | 12/1995 | Gumpp | |
| 5,724,119 A | 3/1998 | Leight | |
| D393,933 S | 4/1998 | Huh | |
| 5,752,280 A | 5/1998 | Hill | |
| D398,421 S | 9/1998 | Crafoord | |
| D421,116 S | 2/2000 | Mattila | |
| 6,032,297 A | 3/2000 | Barthold et al. | |
| 6,035,451 A | 3/2000 | Burns et al. | |
| 6,055,983 A | 5/2000 | Metzger | |
| 6,102,033 A | 8/2000 | Baribeau | |
| D433,751 S | 11/2000 | Reischel | |
| 6,154,881 A | 12/2000 | Lee | |
| 6,185,739 B1 | 2/2001 | Verkic et al. | |
| 6,260,197 B1 | 7/2001 | Hoogewind | |
| 6,264,392 B1 | 7/2001 | Wise | |
| D449,103 S | 10/2001 | Legare | |
| 6,298,498 B1 | 10/2001 | Burns et al. | |
| 6,341,382 B1 | 1/2002 | Ryvin et al. | |
| 6,367,085 B1 * | 4/2002 | Berg | A42B 3/145 128/201.24 |
| 6,393,617 B1 | 5/2002 | Paris | |
| D465,568 S | 11/2002 | Petherbridge | |
| D467,489 S | 12/2002 | Rubinson | |
| D489,492 S | 5/2004 | Wu | |
| D492,559 S | 7/2004 | Itano | |
| 6,782,558 B1 | 8/2004 | Keen, Sr. et al. | |
| 6,973,672 B2 | 12/2005 | Huh | |
| 6,973,676 B1 | 12/2005 | Simpson | |
| D520,856 S | 5/2006 | Osiecki | |
| D520,859 S | 5/2006 | Osiecki | |
| D521,190 S | 5/2006 | Wu | |
| 7,089,603 B2 | 8/2006 | Ketterer et al. | |
| D530,185 S | 10/2006 | Osiecki | |
| 7,120,939 B1 | 10/2006 | Howard | |
| 7,178,932 B1 | 2/2007 | Buckman | |
| D543,828 S | 6/2007 | Strutin-Belinoff | |
| 7,284,281 B2 | 10/2007 | Huh | |
| D557,128 S | 12/2007 | Sawdon | |
| 7,308,719 B2 | 12/2007 | Huh | |
| 7,318,437 B2 | 1/2008 | Gunaratnam | |
| 7,441,282 B2 * | 10/2008 | Heine | A61B 90/50 2/418 |
| D584,003 S | 12/2008 | Juhlin | |
| D589,654 S | 3/2009 | Juhlin | |
| D589,776 S | 4/2009 | Camp | |
| D590,232 S | 4/2009 | Demers | |
| 7,534,005 B1 | 5/2009 | Buckman | |
| D600,094 S | 9/2009 | Hwang | |
| D602,639 S | 10/2009 | Ho | |
| D617,459 S | 6/2010 | Bogue | |
| D626,963 S | 11/2010 | Kim | |
| D632,944 S | 2/2011 | Kang | |
| D635,721 S | 4/2011 | Cheng | |
| 8,056,152 B2 | 11/2011 | Brace | |
| D654,224 S | 2/2012 | Wu | |
| D654,634 S | 2/2012 | Wu | |
| 8,214,920 B1 | 7/2012 | Edgar | |
| D667,173 S | 9/2012 | Juhlin et al. | |
| 8,286,269 B2 | 10/2012 | Springer et al. | |
| 8,336,114 B1 | 12/2012 | Lee | |
| D674,150 S | 1/2013 | Juhlin et al. | |
| D674,153 S | 1/2013 | Daniels et al. | |
| D676,551 S | 2/2013 | Desai | |
| 8,381,312 B2 | 2/2013 | Seo | |
| 8,387,162 B2 | 3/2013 | Huh | |
| D684,252 S | 6/2013 | Okada | |
| 8,584,265 B2 | 11/2013 | Lilenthal et al. | |
| 8,627,517 B2 | 1/2014 | Ahlgren et al. | |
| D710,546 S * | 8/2014 | Wu | D29/102 |
| 8,826,464 B2 | 9/2014 | Wu | |
| D722,259 S | 2/2015 | Conner | |
| 8,990,963 B2 | 3/2015 | Matthews | |
| 9,038,198 B2 | 5/2015 | Feinberg | |
| D735,949 S | 8/2015 | Dion | |
| D735,951 S | 8/2015 | Birath | |
| 9,125,448 B2 | 9/2015 | Klotz | |
| 9,155,923 B2 | 10/2015 | Proctor | |
| D742,596 S | 11/2015 | Peng | |
| D743,629 S | 11/2015 | Peng | |
| D747,556 S | 1/2016 | Fujita | |
| D749,796 S | 2/2016 | Barmore | |
| 9,427,040 B2 * | 8/2016 | Leyland | A42B 3/04 |
| D767,829 S * | 9/2016 | Wu | D29/122 |
| 9,516,911 B2 | 12/2016 | Happel | |
| 9,706,805 B2 * | 7/2017 | Pereira | A42B 1/24 |
| 9,956,118 B2 | 5/2018 | Sernfalt | |
| 2003/0135911 A1 | 7/2003 | Wang-Lee | |
| 2004/0179149 A1 | 9/2004 | Wang-Lee | |
| 2006/0080761 A1 | 4/2006 | Huh | |
| 2006/0225187 A1 | 10/2006 | Wu | |
| 2007/0050892 A1 | 3/2007 | Charles | |
| 2007/0113318 A1 | 5/2007 | Weston | |
| 2007/0220649 A1 | 9/2007 | Huh | |

(56) References Cited

U.S. PATENT DOCUMENTS

| | | |
|---|---|---|
| 2007/0245467 A1 | 10/2007 | Lilenthal |
| 2008/0060102 A1 | 3/2008 | Matthews |
| 2009/0089908 A1 | 4/2009 | Huh |
| 2009/0210989 A1 | 8/2009 | Becker et al. |
| 2009/0235420 A1 | 9/2009 | Chiang |
| 2010/0050325 A1* | 3/2010 | Wang-Lee ............ A42B 3/145 2/418 |
| 2010/0212058 A1 | 8/2010 | Wanhainen |
| 2010/0229274 A1 | 9/2010 | Ahlgren |
| 2010/0229286 A1* | 9/2010 | Ahlgren ................ A42B 3/142 2/416 |
| 2010/0235971 A1* | 9/2010 | Ahlgren .................. A42B 3/14 2/416 |
| 2010/0287676 A1 | 11/2010 | Seo |
| 2010/0294270 A1 | 11/2010 | Curran |
| 2011/0101890 A1 | 5/2011 | Robinson |
| 2011/0167542 A1* | 7/2011 | Bayne ..................... A42B 3/14 2/416 |
| 2011/0179541 A1 | 7/2011 | Wright |
| 2011/0219506 A1 | 9/2011 | Uttrachi |
| 2011/0265790 A1 | 11/2011 | Walker et al. |
| 2012/0144565 A1* | 6/2012 | Huh ....................... A42B 3/145 2/421 |
| 2012/0144567 A1* | 6/2012 | Huh ......................... A42B 3/14 2/424 |
| 2012/0291172 A1 | 11/2012 | Wills |
| 2013/0111653 A1* | 5/2013 | Huh ......................... A42B 3/14 2/421 |
| 2013/0152919 A1 | 6/2013 | Billingsley et al. |
| 2014/0007312 A1 | 1/2014 | Wright |
| 2014/0208476 A1 | 7/2014 | Chen |
| 2014/0298557 A1 | 10/2014 | Townsend, Jr. |
| 2015/0143618 A1 | 5/2015 | Pereira et al. |
| 2015/0143669 A1* | 5/2015 | Pereira ................... A42B 1/24 24/3.12 |
| 2015/0264992 A1 | 9/2015 | Happel |
| 2015/0359680 A1 | 12/2015 | Gardner |
| 2016/0081856 A1 | 3/2016 | Hofer-Kraner |
| 2016/0183622 A1 | 6/2016 | Patel |
| 2016/0360821 A1 | 12/2016 | Benton |
| 2017/0112226 A1 | 4/2017 | Watkins |

FOREIGN PATENT DOCUMENTS

| | | |
|---|---|---|
| CN | 101815556 A | 8/2010 |
| CN | 101827538 A | 9/2010 |
| CN | 102370541 A | 3/2012 |
| CN | 102525731 A | 7/2012 |
| CN | 102551956 A | 7/2012 |
| CN | 203264074 U | 11/2013 |
| EP | 2 184 039 A1 | 5/2010 |
| EP | 2 462 825 A2 | 6/2012 |
| EP | 2 462 826 A2 | 6/2012 |
| EP | 2 907 401 A1 | 8/2015 |
| WO | 2008/025083 A1 | 3/2008 |
| WO | 2009/048829 A1 | 4/2009 |
| WO | 2009/048836 A1 | 4/2009 |
| WO | 2014160149 A2 | 10/2014 |
| WO | 2015195495 A1 | 12/2015 |

OTHER PUBLICATIONS

International Search Report and Written Opinion for PCT/US2015/035714 dated Oct. 8, 2015, 11 pages.
International Search Report and Written Opinion for PCT/US2015/035713 dated Oct. 27, 2015, 17 pages.
International Search Report and Written Opinion for PCT/US2015/065213 dated Mar. 16, 2016, 13 pages.
Inyopools.com, How to set up the zodiac T5 suction cleaner through your skimmer, https://webarchive.org/web/20130627095500/http://www.inyopools.com/HowToPage/How-to-set-up-the-zodiac0t5-cleaner-through-your-skimmer.aspx, Jun. 27, 2013, Retreived via Wayback Machine on Apr. 19, 2016.
Miller 9400i welding helmet with an integrated grind shield, published at least as early as Jun. 16, 2014, 1 page.
Speedglas 9100FX welding helmet with an integrated grind shield, published at least as early as Jun. 16, 2014, 1 page.
Speedglas 9002X Flexview welding helmet with an integrated grind shield, published at least as early as Jun. 16, 2014, 1 page.
Miller 9400i PAPR welding helmet with powered air purifying system, belt mounted blower with breathing tube connecting to manifold inside head assembly, published at least as early as Jun. 16, 2014, 1 page.
Speedglas 9100X Air Adflo welding helmet with airflow delivery mechanism, published at least as early as Jun. 16, 2014, 1 page.
Speedglas 9100FX Air Adflo welding helmet with airflow delivery mechanism, published at least as early as Jun. 16, 2014, 1 page.
Miller headgear for a welding helmet, published at least as early as Jun. 16, 2014, 1 page.
Speedglas headgear for a welding helmet, published at least as early as Jun. 16, 2014, 1 page.
Official Action for Canadian Patent Application No. 2,951,844 dated Jan. 5, 2018, 4 pages.
Communication pursuant to Rule 94(3) EPC issued for EP 15 7 2 8 713.7 dated Jul. 11, 2018, 5 pages.

* cited by examiner

HEADGEAR FOR PROTECTIVE HEADWEAR

RELATED APPLICATIONS

The present application claims the priority benefit of co-pending U.S. Provisional Patent Application Ser. No. 62/012,483, filed Jun. 16, 2014, the content of which is incorporated by reference herein.

FIELD OF THE INVENTION

The present disclosure generally relates to protective headwear and, more particularly, to headgear within protective headwear for supporting the protective headwear on a wearer's head.

BACKGROUND

Protective headwear typically includes headgear within the headwear to engage a wearer's head and support the protective headwear upon the wearer's head. Conventional headgear is uncomfortable, unstable on a wearer's head, and poor at accommodating different size heads.

SUMMARY

Thus, a need exists for headgear that resolves one or more of these deficiencies.

In one aspect, it is desirable to have headgear that is comfortable, stable, and capable of adequately accommodating heads of varying size.

In one aspect, a headgear for protective headwear is provided and includes a pivotal forehead strap.

In one aspect, a headgear for protective headwear is provided and includes a forehead strap including a first member, a second member space-apart from the first member and a cavity between the first member and the second member.

In one aspect, a headgear for engaging and supporting protective headwear on a wearer's head is provided. The headgear may include a first side member on a first side of the headgear, a second side member on a second side of the headgear, and a forehead strap pivotally coupled to and extending between the first and second side members. The forehead strap may be configured to engage a wearer's forehead with the headgear worn by a wearer. The headgear may also include a second strap coupled to and extending between the first and second side members.

In one aspect, the second strap may be rigidly coupled to the first and second side members.

In one aspect, the second strap may include a first end rigidly and non-rotatably coupled to the first side member and a second end rigidly and non-rotatably coupled to the second side member.

In one aspect, the second strap may be pivotally coupled to and extend between the first and second side members.

In one aspect, the forehead strap may rotate within an angle of about 1 degree to about 90 degrees, and the second strap may rotate within an angle of about 1 degree to about 90 degrees.

In one aspect, the forehead strap may rotate within an angle of about 5 degrees to about 45 degrees, and the second strap may rotate within an angle of about 5 degrees to about 45 degrees.

In one aspect, the forehead strap may rotate within an angle of about 15 degrees, and the second strap may rotate within an angle of about 15 degrees.

In one aspect, the second strap may be a top strap configured to extend over a top of a wearer's head.

In one aspect, the headgear may further include a third strap coupled to and extending between the first and second side members. The second strap may be positioned between the forehead strap and the third strap.

In one aspect, one of the second strap and the third strap may be pivotally coupled to the first and second side members, and the other of the second strap and the third strap may be rigidly and non-pivotally coupled to the first and second side members.

In one aspect, the second strap may be pivotally coupled to the first and second side members, and the third strap may be rigidly and non-pivotally coupled to the first and second side members.

In one aspect, the third strap may be unitarily formed as one-piece with the first and second side members.

In one aspect, the second strap may be a top strap configured to extend over and engage a top of a wearer's head and the third strap may be a rear strap configured to extend behind and engage a rear of a wearer's head.

In one aspect, the forehead strap may rotate within an angle of about 1 degree to about 90 degrees.

In one aspect, the forehead strap may rotate within an angle of about 5 degrees to about 45 degrees.

In one aspect, the forehead strap may rotate within an angle of about 15 degrees.

In one aspect, the forehead strap may be snap-fit to the first and second side members.

In one aspect, an aperture may be defined near each end of the forehead strap. Each of the first and second side members may include a pair of resilient projections extending therefrom. The pair of resilient projections extending from the first side member may insert into one of the apertures on one end of the forehead strap and the pair of resilient projections extending from the second side member may insert into the other one of the apertures in the other end of the forehead strap.

In one aspect, the headgear may further include a limiting member engageable by the forehead strap to limit pivoting of the forehead strap.

In one aspect, the limiting member may extend from one of the first and second side members and may be engageable by an edge of the forehead strap.

In one aspect, the limiting member may be engageable by a top edge and a bottom edge of the forehead strap to limit pivoting of the forehead strap in two directions.

In one aspect, a protective headwear is provided and includes a shell, a shield coupled to the shell and configured to allow at least partial viewing there through by a wearer of the protective headwear, and a headgear pivotally coupled to the shell. The headgear is configured to engage a wearer's head to support the shell relative to the wearer's head and facilitate pivoting of the shell relative to the headgear between a downward position and an upward position. The headgear includes a first side member on a first side of the headgear, a second side member on a second side of the headgear, and a forehead strap pivotally coupled to and extending between the first and second side members. The forehead strap is configured to engage a wearer's forehead with the headgear worn by a wearer. The headgear also includes a second strap coupled to and extending between the first and second side members, and a third strap coupled to and extending between the first and second side members.

The second strap is between the forehead strap and the third strap. One of the second strap and the third strap is pivotally coupled to the first and second side members, and the other one of the second strap and the third strap is rigidly and non-pivotally coupled to the first and second side members.

BRIEF DESCRIPTION OF THE DRAWINGS

The disclosure can be better understood with reference to the following drawings and description. The components in the figures are not necessarily to scale, emphasis instead being placed upon illustrating the principles of the disclosure.

DETAILED DESCRIPTION

Figure 1:
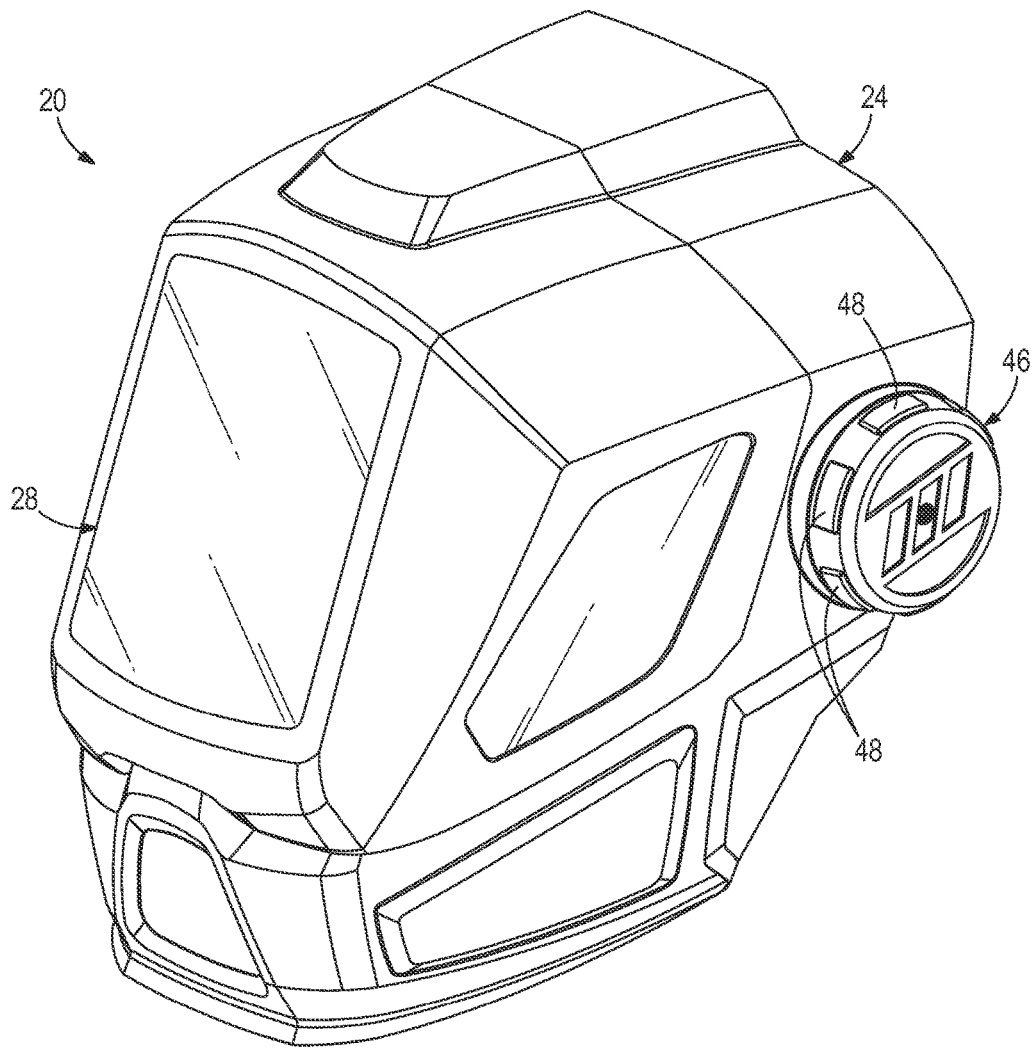
FIG. 1 is a top, front perspective view of one example of a protective headwear, according to one aspect of the present disclosure.

Referring to FIG. 1, one example of protective headwear 20 is illustrated. In this illustrated example, the protective headwear 20 is a welding helmet. The welding helmet 20 includes an outer shell 24, a first shield 28, a second shield (beneath the first shield 28 and not shown), and headgear 36 (see FIG. 2) positioned within the outer shell 24. The first shield 28 may be a welding shield and is coupled to the outer shell 24 over the second shield. The first shield 28 is tinted or otherwise darkened in order to inhibit damage to a wearer's eyes while performing a welding process. The second shield is coupled to the outer shell 24 beneath the first shield 28 and is less tinted or more transparent than the first shield 28. In one example, the second shield has no tinting or darkening and is completely transparent. The second shield may be referred to as a grinding shield.

Figure 2:
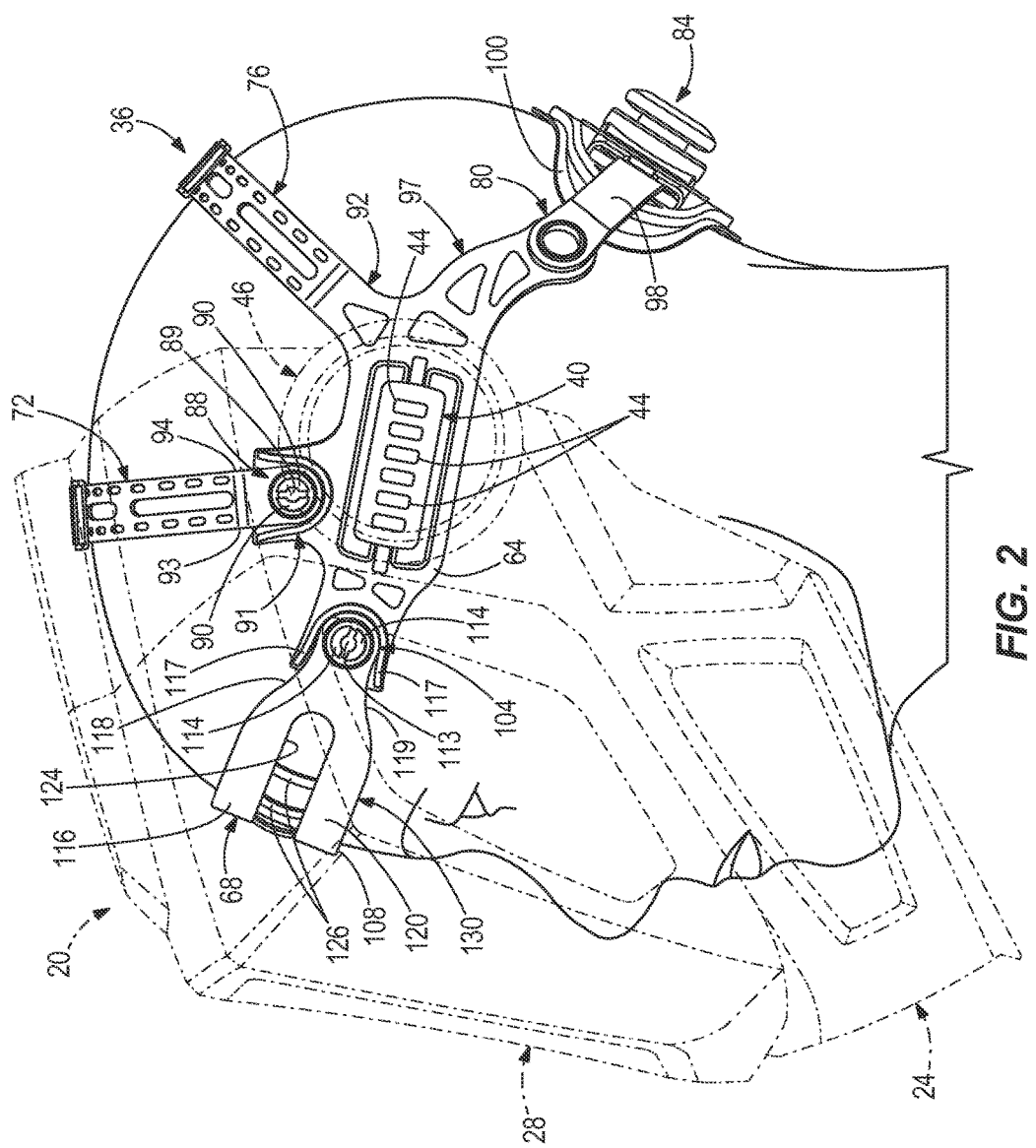
FIG. 2 is a side view of one example of headgear that may be included in the protective headwear shown in FIG. 1, according to one aspect of the present disclosure.
Figure 3:
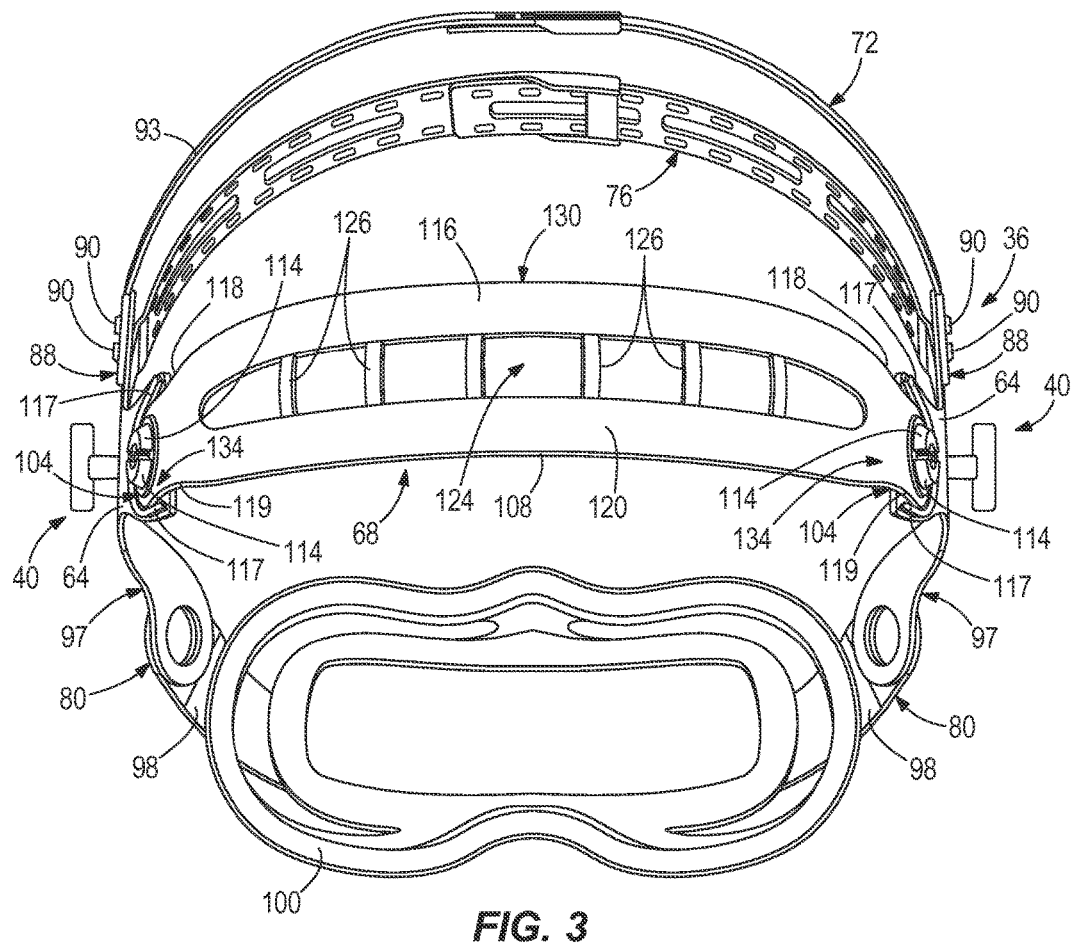
FIG. 3 is a front view of the headgear shown in FIG. 2, according to one aspect of the present disclosure.
Figure 4:
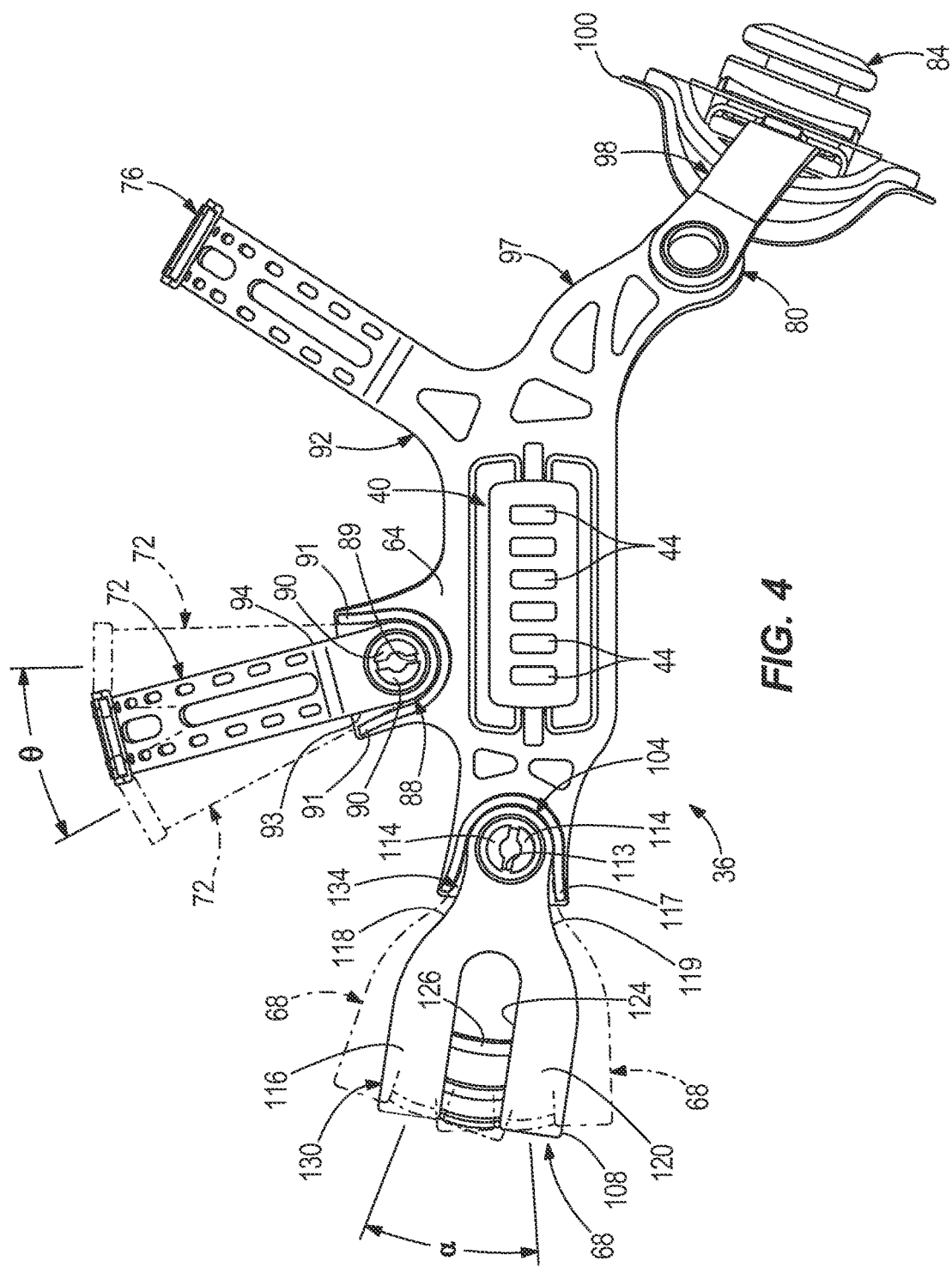
FIG. 4 is a side view of the headgear shown in FIG. 2 with a forehead strap being pivotal within a first range and a top strap being pivotal within a second range, according to one aspect of the present disclosure.

Referring now to FIGS. 2-4, one example of headgear 36 is illustrated. One side of the headgear 36 is illustrated in FIGS. 2 and 4, but it should be understood that the headgear 36 may be a substantial mirror image about a vertical plane extending through a center of the headgear 36 (and a wearer's head when the headgear 36 is worn). In other words, the headgear 36 may be symmetrical on both sides of a wearer's head as illustrated in FIG. 3. The headgear 36 is capable of coupling to the exemplary protective headwear 20 illustrated in FIG. 1 or the headgear 36 may be coupled to other types of protective headwear 20. For example, the headgear 36 may be coupled to hard hats, bicycle helmets, or any other type of headwear capable of providing protection to a wearer's head. The headgear 36 is capable of engaging a wearer's head and supporting the protective headwear 20 on the wearer's head. The headgear 36 may be coupled to the outer shell 24 of the protective headwear 20 in a variety of manners such as, for example, movably coupled, pivotally coupled, rigidly coupled, unitarily formed with, among other manners.

With continued reference to FIGS. 2-4, the headgear 36 includes a coupling member 40 on each side of the headgear 36 for coupling to the outer shell 24 on both sides of the outer shell 24. Each coupling member 40 has a plurality of mounting locations 44 to which the outer shell 24 may be selectively coupled as desired. The outer shell 24 is coupled to one mounting location 44 at a time on each side and remains rigidly coupled to those mounting locations 44 until the outer shell 24 is actively decoupled from the headgear 36. The various mounting locations 44 provide a wearer with the ability to adjust the outer shell 24 relative to the wearer's head.

Referring to FIGS. 1 and 2, the protective headwear 20 includes an actuator 46 on each side of the outer shell 24 that is rotatable relative to the outer shell 24. The outer shell 24 is capable of rotating relative to the headgear 36 between a down, operable position as shown in FIG. 1, in which the protective headwear 20 covers a wearer's face and eyes to protect them during a welding or other operation, and an upward, inoperable position, in which the outer shell 24 is rotated upward away from the wearer's eyes and face to expose them while a wearer may not be performing an operation. The actuators 46 are adjustable to provide varying quantities of resistance to movement of the outer shell 24 relative to the headgear 36. In some instances, a wearer may wish to have little to no resistance to rotation of the outer shell 24 between the upward and downward positions and in other instances a wearer may wish to have more or significant resistance to rotation of the outer shell 24 relative to the headgear 36. Each actuator 46 is generally cylindrical in shape, includes a plurality of projections 48 around a circumference of the actuators 46 to assist with gripping of the actuators 46, and is threadably coupled to the headgear 36. Rotating the actuators 46 in one direction tightens or increases resistance between the outer shell 24 and the headgear 36, thereby making it more difficult to rotate the outer shell 24 relative to the headgear 36. Rotating the actuators 46 in a second or opposite direction loosens or decreases the resistance between the outer shell 24 and the headgear 36, thereby making it easier to rotate the outer shell 24 relative to the headgear 36.

Referring again to FIGS. 2-4, the headgear 36 also includes a side member 64 on each side of the headgear 36, a forehead strap 68, a top strap 72, a rear strap 76, an occipital strap 80 and a tightening member 84 coupled to the occipital strap 80.

The top strap 72 is pivotally coupled at its ends 88 to respective side members 64 and is positioned to extend over a crown or top of a wearer's head. Protective headwear 20 is commonly used in non-level orientations such as, for example, a downward angle (e.g., during welding, the welder is looking downward and forward toward the welding area), an upward angle (e.g., a wearer may be looking upward and overhead), etc. In such non-level orientations, the top strap 72 may minimize shifting of the protective headwear 20 relative to the wearer's head as a result of the top strap 72 extending over the crown or top of the wearer's head. The top strap 72 may be pivotally coupled to the side members 64 in a variety of manners and all of such possibilities are intended to be within the spirit and scope of the present disclosure. In the illustrated example, the top strap 72 is snap-fit to the side members 64 in a manner that allows pivoting of the top strap 72 relative to the side members 64. In this example, an aperture 89 is defined near each end 88 of the top strap 72 and a pair of spaced-apart, resilient projections 90 extend from each of the side members 64. The projections 90 are moveable relative to each other and may be pressed together or toward each other to allow the projections 90 to insert into a respective one of the apertures 89 defined in an end 88 of the top strap 72. When the protections 90 are pressed together, the projections 90 are sufficiently close together to be smaller than the respective aperture 89 and insert into the aperture 89. The resiliency of the two projections 90 allow the two projections 90 to move toward their at rest position when a user ceases to press the projections 90 together. The two projections 90 return to a size larger than the respective aperture 89 of the top strap 72 to inhibit the top strap 72 from being removed from the side members 64. This configuration of apertures 89 and projections 90 facilitate rotation of the top strap 72 relative to the side members 64.

The headgear 36 also includes a limiting member or stop 91 associated with each end 88 of the top strap 72 to limit rotation of the top strap 72 relative to the side members 64. The limiting member 91 may have any configuration, may be positioned on the top strap 72 and/or the side members 64, and may limit rotation of the top strap 72 within any range of movement and all of such possibilities are intended to be within the spirit and scope of the present disclosure. In the illustrated example, each limiting member 91 comprises a projection extending from the respective side member 64 and positioned to engage opposite longitudinal edges 93, 94 of the top strap 72. The projection 91 engages a front edge 93 of the top strap 72 to limit rotation of the top strap 72 toward a front of the headgear 36 and engages a rear edge 94 of the top strap 72 to limit rotation of the top strap 72 toward a rear of the headgear 36. In the illustrated example, each projection 91 extends uninterrupted (or contiguous) around the end 88 of the top strap 92 about 270 degrees to engage both the front and rear edges 93, 94 of the top strap 72. In another example, the headgear 36 may include multiple limiting members at each end 88 of the top strap 72. For example, the headgear 36 may include a first limiting member to engage the front edge 93 of the top strap 72 and a second limiting member to engage the rear edge 94 of the top strap 72. This example with multiple limiting members may be employed at both ends 88 of the top strap 72. In another example, the headgear 36 may include a limiting member at only one end 88 of the top strap 72, thereby limiting rotation of the top strap 72 at only one end 88.

With particular reference to FIG. 4, the limiting members 91 associated with the top strap 72 (one limiting member at each end 88 in the illustrated embodiment) are configured to allow rotation of the top strap 72 within angle θ. The angle θ may be any angle and all of such possibilities are intended to be within the intended spirit and scope of the present disclosure. In one example, the angle θ may be about 15 degrees. In another example, the angle θ may be between about 5 degrees and about 30 degrees. In another example, the angle θ may be between about 1 degree and about 90 degrees. The top strap 72 is capable of being rotated between any angle or any range of angles and all of such possibilities are intended to be within the spirit and scope of the present disclosure.

With reference to FIGS. 2-4, the rear strap 76 is rigidly coupled at its ends 92 to respective side members 64 (i.e., non-rotatable) and is positioned to extend around a rear of a wearer's head. In another example, the rear strap 76 may be pivotally coupled at its ends 92 to respective side members 64. In such an example, the rear strap 76 may rotate between any range of angles and may be limited in rotation in any manner, including the limiting members described above with respect to the top strap 72, and all of such possibilities are intended to be within the spirit and scope of the present disclosure. The top strap 72 and the rear strap 76 are oriented in positions relative to each other to minimize shifting of the protective headwear 20 on a wearer's head.

The two occipital straps 80, one on each side of the headgear 36, extend from the side members 64, drop down below the rear strap 76, and wrap around or extend along an occipital crest of a wearer, then extend under the occipital crest. The positions of the occipital straps 80 allow pressure originating from the protective headwear 20 to be applied to bony structure (e.g., the occipital bone and crest of a skull) of the wearer's head where the wearer has less of a perception of pressure than on soft tissue of the wearer's head.

In the illustrated example, the occipital straps 80 may be compliant to the wearer's head. The occipital straps 80 may be made of a variety of different materials and have a variety of shapes, as long as the occipital straps 80 are compliant. In one example, each occipital strap includes a first portion 97 rigidly coupled to the side member 64 and a second portion 98 pivotally coupled to the first portion 97 at ends of the first portion 97 and the second portion 98. In one example, the first portions 97 of the occipital strap 80 may be unitarily formed as one-piece with the side members 64. The second portions 98 of the occipital strap 80 are rotatable relative to the respective first portions 97 between any range of angles and are coupled to the tightening member 84. Each of the first portions 97 of the occipital strap 80 extend backwards and downwards from the respective side member 64.

In another example, the side members 64 may extend rearward and downward, and the occipital straps 80 may be pivotally coupled to ends of respective side members 64. In this example, the tightening member 84 is coupled to the occipital straps 80 and the occipital straps 80 are rotatable relative to the side members 64 between any range. If this example is compared to the previous example, the first portions 97 of the occipital strap 80 in the previous example would be considered part of the side members 64 and the second portions 98 of the previous example would be considered the occipital straps 80 in this example.

With continued reference to FIGS. 2-4, the headgear 36 further includes a pad 100 coupled to at least one of the occipital straps 80 and/or the tightening member 84 and positioned at a rear of the headgear 36. The pad 100 is capable of engaging a rear of the wearer's head to provide comfort and further support. When the tightening member 84 is tightened, the pad 100 may rise up and under the occipital crest of the wearer's head to secure the headgear 36 in place using the natural geometry of the wearer's head.

Referring to FIGS. 2-4, the forehead strap 68 is pivotally coupled to the remainder of the headgear 36. The forehead strap 68 includes two ends 104 with both ends 104 pivotally coupled to respective side members 64 at a high forehead position. Human heads have a variety of forehead slopes and the pivoting forehead strap 68 accommodates such varying forehead slopes. As a wearer begins to place the headgear 36 on his/her head, the wearer will pull the headgear 36 down onto his/her head, the forehead strap 68 will slide down the wearer's forehead, and will terminate sliding down the wearer's head at an appropriate point on the wearer's forehead based on the slope of the wearer's forehead. It is likely that the remainder of the headgear 36 is not completely down and supported upon the wearer's head when the forehead strap 68 is in this position. The pivoting ends 104 of the forehead strap 68 allow the remainder of the headgear 36 to continue to move downward until the top and rear straps 72, 76 engage the wearer's head and the headgear 36 is supported on the wearer's head. The pivoting forehead strap 68 will lie flat against a wearer's forward and evenly distribute pressure to the wearer's forehead, rather than apply a significant quantity of pressure at a single point or edge. In some instances of conventional headgear, the forehead strap, the side members and/or the rear strap are the same, unitary strap. With such a conventional design, the conventional forehead strap would have prevented the headgear from settling completely onto a wearer's head and a front bottom edge of the conventional forehead strap would dig into the wearer's forehead. The pivotal forehead strap 68 of the present disclosure also inhibits a front lower edge 108 of the forehead strap 68 from digging into the wearer's head.

As can be seen in FIGS. 2-4, the forehead strap 68 is pivotally coupled at its ends 104 to respective side members 64 and is positioned to extend over a forehead of a wearer's head. The forehead strap 68 may be pivotally coupled to the side members 64 in a variety of manners and all of such possibilities are intended to be within the spirit and scope of the present disclosure. In the illustrated example, the forehead strap 68 is snap-fit to the side members 64 in a manner that allows pivoting of the forehead strap 68 relative to the side members 64. In this example, an aperture 113 is defined in each end 104 of the forehead strap 68 and a pair of spaced-apart, resilient projections 114 extend from each of the side members 64. The projections 114 are moveable relative to each other and may be pressed together or toward each other to allow the projections 114 to insert into a respective one of the apertures 113 defined in an end 104 of the forehead strap 68. When the projections 114 are pressed together, the projections 114 are sufficiently close together to be smaller than the aperture 113, thereby facilitating insertion into the aperture 113. The resiliency of the two projections 114 allow the two projections 114 to return toward their at rest position when a user ceases to press the projections 114 together. The two projections 114 return to a size larger than the respective aperture 113 of the forehead strap 68 to inhibit the forehead strap 68 from being removed from the side members 64. This configuration of apertures 113 and projections 114 facilitate rotation of the forehead strap 68 relative to the side members 64, while also inhibiting removal of the forehead strap 68 from the side members 64.

The headgear 36 also includes a limiting member or stop 117 associated with each end 104 of the forehead strap 68 to limit rotation of the forehead strap 68 relative to the side members 64. The limiting members 117 may have any configuration, may be positioned on the forehead strap 68 and/or the side members 64, and may limit rotation of the forehead strap 68 between any range of movement and all of such possibilities are intended to be within the spirit and scope of the present disclosure. In the illustrated example, each limiting member 117 comprises a projection extending from the respective side member 64 and is positioned to engage opposite longitudinal edges 118, 119 of the forehead strap 68. The projection 117 engages a bottom edge 119 of the forehead strap 68 to limit rotation of the forehead strap 68 downward and engages a top edge 118 of the forehead strap 68 to limit rotation of the forehead strap 68 upward. In the illustrated example, each projection 117 extends uninterrupted (or contiguous) around the respective end 104 of the forehead strap 68 about 270 degrees to engage both the top and bottom edges 118, 119 of the forehead strap 68. In another example, the headgear 36 may include multiple limiting members 117 at each end 104 of the forehead strap 68. For example, the headgear 36 may include a first limiting member to engage the bottom edge 119 of the forehead strap 68 and a second limiting member to engage the top edge 118 of the forehead strap 68. This example with multiple limiting members may be employed at both ends 104 of the forehead strap 68. In another example, the headgear 36 may include a limiting member 117 at only one end 104 of the forehead strap 68, thereby limiting rotation of the forehead strap 68 at only one end 104.

With particular reference to FIG. 4, the limiting members 117 associated with the forehead strap 68 (one limiting member at each end 104 in the illustrated embodiment) are configured to allow rotation of the forehead strap 68 between angle α. The angle α may be any angle and all of such possibilities are intended to be within the intended spirit and scope of the present disclosure. In one example, the angle α may be about 15 degrees. In another example, the angle α may be between about 5 degrees and about 30 degrees. In another example, the angle α may be between about 1 degree and about 90 degrees. The forehead strap 68 is capable of being rotated between any angle or any angle range and all of such possibilities are intended to be within the spirit and scope of the present disclosure.

In some examples, the pivoting forehead strap 68 may eliminate the need to include a tightening member that provides additional pressure to secure the headgear 36 to a wearer's head. In one example, the forehead strap 68 may include padding or other soft material on an interior surface thereof configured to engage a wearer's forehead and provide additional comfort. In one example, the pivoting forehead strap 68 provides a self-adjusting feature that allows a wearer to adjust or move the protective headwear 20 and headgear 36 relative to their head and the pivoting forehead strap 68 accommodates that movement to resettle the headgear 36 and the protective headwear 20 on the wearer's head.

With continued reference to FIGS. 2-4, the forehead strap 68 is a split forehead strap 68 including an upper member 116, a lower member 120 and a space or cavity 124 between the upper member 116 and the lower member 120. The split forehead strap 68 distributes pressure or force applied to a wearer's forehead by the protective headwear 20 over a larger surface area, while also having minimal contact area with the wearer's forehead as a result of the cavity 124. Additionally, air can access a wearer's forehead through the cavity 124, thereby increasing the comfort of a wearer while wearing the protective headwear 20 and the headgear 36.

In the illustrated example, the forehead strap 68 is a unitarily formed one-piece member including two pivots or pivot points, one at each end thereof, and the cavity 124 being defined between the upper and lower members 116, 120. The forehead strap 68 also includes at least one support member 126 extending between the upper and lower members 116, 120. The at least one member 126 may provide stability or rigidity between the upper and lower members 116, 120. In the illustrated example, the forehead strap 68 includes a plurality of members 126 extending between the upper and lower members 116, 120. The forehead strap 68 may include any number of members 126 extending between the upper and lower members 116, 120 and all of such possibilities are intended to be within the spirit and scope of the present disclosure.

With continued reference to FIGS. 2-4, the forehead strap 68 is wider 130 in a middle of the forehead strap 68 and narrower 134 near each end of the forehead strap 68. In one example, a size of the wider portion 130 corresponds to a size of the cavity 124. In one example, the wider portion 130 is about a same length as a length of the cavity 124. In another example, the wider portion 130 is slightly longer than a length of the cavity 124.

Figure 5:
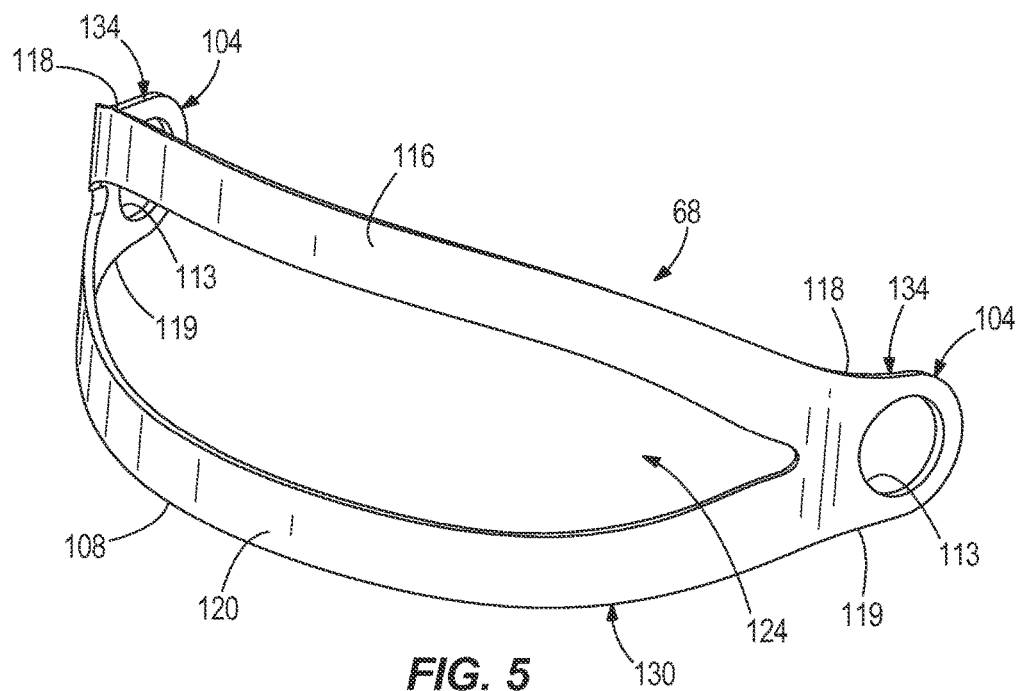
FIG. 5 is a top, front perspective view of another example of a forehead strap that is capable of being used with the headgear shown in FIG. 2, according to one aspect of the present disclosure.

Referring now to FIG. 5, another example of a forehead strap 68 is illustrated. The upper member 116, lower member 120 and cavity 124 have different shapes and configurations than the forehead strap 68 illustrated in FIGS. 2-4. However, the forehead strap 68 in FIG. 5 is still a pivoting forehead strap 68. The forehead strap 68 illustrated in FIG. 5 may be coupled to and pivot relative to the side members 64 in similar manners and alternatives discussed above with respect to the forehead strap 68 illustrated in FIGS. 2-4.

Figure 6:
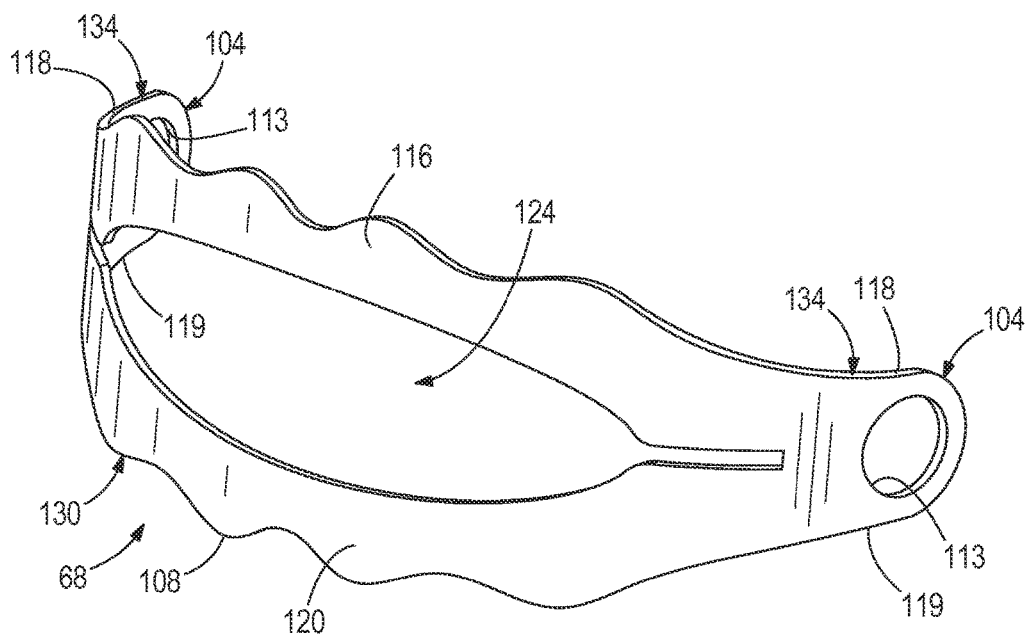
FIG. 6 is a top, front perspective view of another example of a forehead strap that is capable of being used with the headgear shown in FIG. 2, according to one aspect of the present disclosure.

With reference to FIG. 6, another example of a forehead strap 68 is illustrated, and this forehead strap 68 is still a pivoting forehead strap 68, but includes an upper member 116, a lower member 120 and a cavity 124 having different shapes and configurations than the forehead strap 68 illustrated in FIGS. 2-4. The forehead strap 68 illustrated in FIG. 6 may be coupled to and pivot relative to the side members 64 in similar manners and alternatives discussed above with respect to the forehead strap 68 illustrated in FIGS. 2-4.

Figure 7:
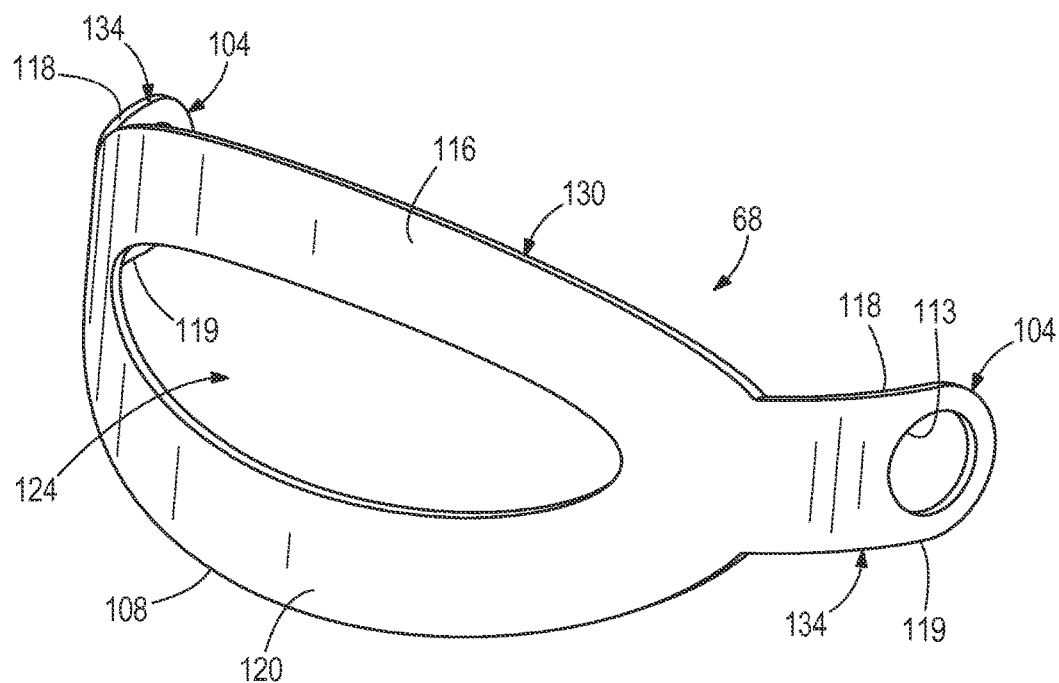
FIG. 7 is a top, front perspective view of another example of a forehead strap that is capable of being used with the headgear shown in FIG. 2, according to one aspect of the present disclosure.

With reference to FIG. 7, another example of a forehead strap 68 is illustrated, and this forehead strap 68 is still a pivoting forehead strap 68, but includes an upper member 116, a lower member 120 and a cavity 124 having different shapes and configurations than the forehead strap 68 illustrated in FIGS. 2-4. The forehead strap 68 illustrated in FIG. 7 may be coupled to and pivot relative to the side members 64 in similar manners and alternatives discussed above with respect to the forehead strap 68 illustrated in FIGS. 2-4.

It should be understood that the forehead strap 68 may have any shape, size, and configuration and still be within the spirit and scope of the present disclosure.

Figure 8:
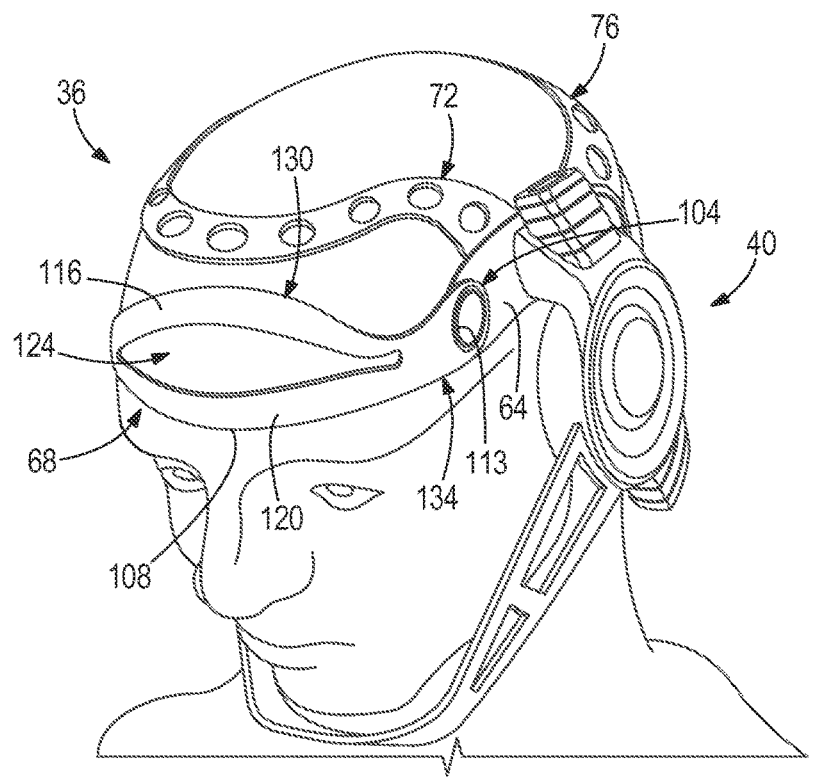
FIG. 8 is a top, front perspective view of another example of a headgear that may be included in the protective headwear shown in FIG. 1, according to one aspect of the present disclosure.
Figure 10:
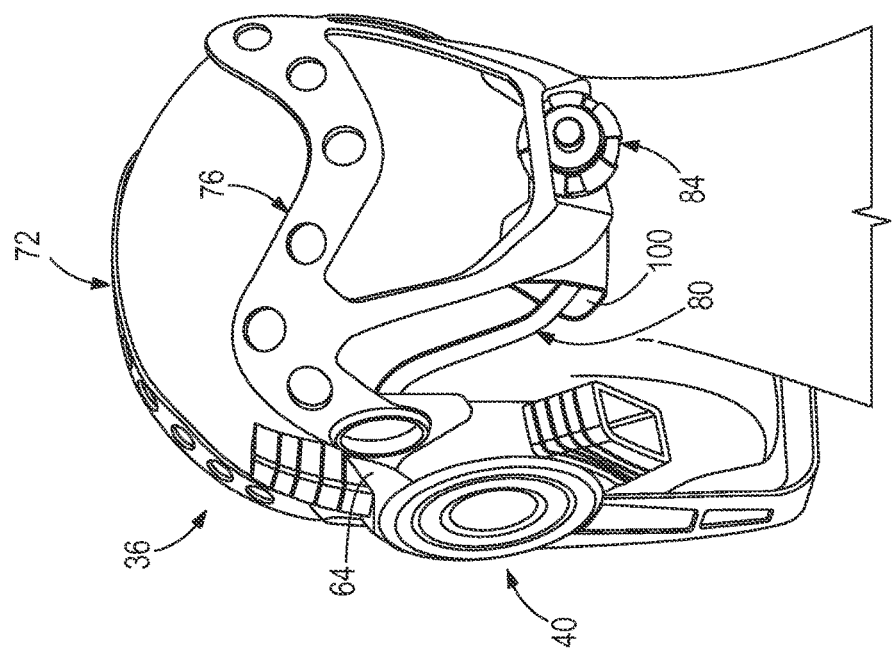
FIG. 10 is a top, rear perspective view of the headgear shown in FIG. 8, according to one aspect of the present disclosure.
Figure 9:
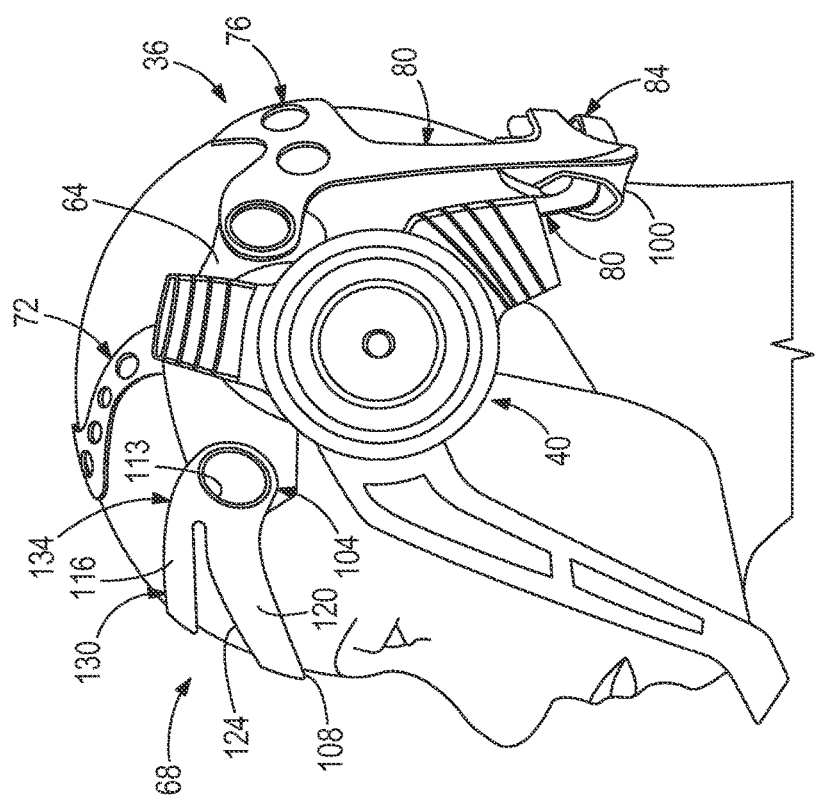
FIG. 9 is a side view of the headgear shown in FIG. 8, according to one aspect of the present disclosure.

Referring now to FIGS. 8-10, another example of a headgear 36 is illustrated. The headgear 36 includes a split forehead strap 68 that pivots about its ends 104, a top strap 72 extending over a crown or top of a wearer's head, a rear strap 76 that extends around a rear of a wearer's head, an occipital strap 80 that is pivotally coupled at its ends to the side members 64, a pad 100 coupled to and around the occipital strap 80 and positioned near a rear of a wearer's head, and a tightening member 84 for tightening the headgear 36 to a wearer's head.

Figure 11:
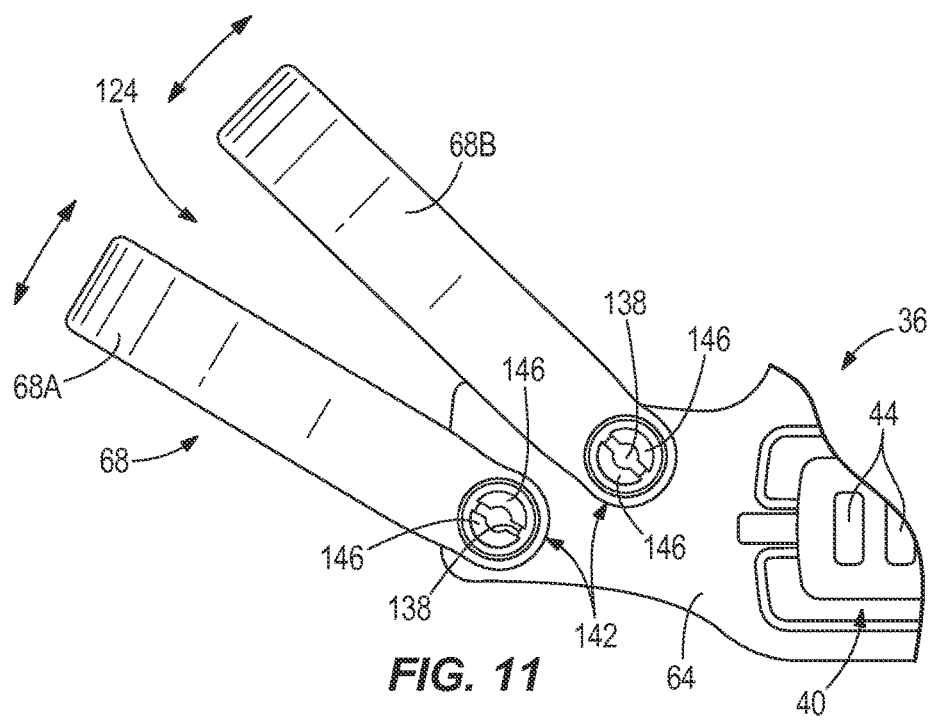
FIG. 11 is a side view of a portion of another example of a headgear capable of being used with the protective headwear shown in FIG. 1, according to one aspect of the present disclosure.

With reference to FIG. 11, another example of a forehead strap 68 is illustrated. One side of the forehead strap 68 and associated components are illustrated in FIG. 11, but it should be understood that the forehead strap 68 and associated components may be a substantial mirror image about a vertical plane extending through a center of the headgear (and a wearer's head when the headgear is worn). In other words, the forehead strap 68 and associated components may be symmetrical on both sides of a wearer's head as illustrated in FIG. 11. In this example, the forehead strap 68 is a pivoting forehead strap and pivots relative to the side members 64. Also, in this example, the forehead strap 68 is comprised of a first forehead strap 68A and a second forehead strap 68B. Both of the first and second forehead straps 68A, 68B are pivotally coupled to the side members 64 and are spaced-apart from one another. This example of the forehead strap 68 includes a space or cavity 124 between the first and second forehead straps 68A, 68B. Similar to the forehead strap 68 illustrated in FIGS. 2-4, each of the first and second forehead straps 68A, 68B define apertures 138 at their ends 142 that cooperate with pairs of projections 146 in order to couple and allow rotation of the first and second forehead straps 68A, 68B to the side members 64. The pairs of projections 146 and ends 142 of the forehead straps 68A, 68B may cooperate in similar manners to that described above in connection with the forehead strap 68 illustrated in FIGS. 2-4.

In this example, the first and second forehead straps 68A, 68B rotate relative to each other and are configured to accommodate various head sizes. The first and second foreheads straps 68A, 68B may rotate between any range of angles. In one example, the first forehead strap 68A may rotate between the same angle as the second forehead strap 68B. In another example, the first forehead strap 68A may rotate between a different angle than the second forehead strap 68B. In the illustrated example, the headgear 36 associated with the first and second forehead straps 68A, 68B does not include any limiting members for engaging and limiting rotation of the first and second forehead straps 68A, 68B. In another example, the headgear 36 associated with the first and second forehead straps 68A, 68B may include a limiting member for each end 142 of both the first and second forehead straps 68A, 68B. In such an example, the headgear 36 would include four limiting members. In another example, the headgear 36 may include a limiting member for only one end 142 of each of the first and second forehead straps 68A, 68B. In such an example, the headgear 36 would include two limiting members. These two limiting members may be on complementary ends 142 of the first and second forehead straps 68A, 68B or opposite ends 142 of the first and second forehead straps 68A, 68B. In another example, only one of the first forehead strap 68A or second forehead strap 68B may have a limiting member(s) associated therewith. In such an example, the limiting member(s) may engage and limit only one of the first or second forehead straps 68A, 68B, while the other of the first or second forehead straps 68A, 68B may be free to rotate.

Figure 12:
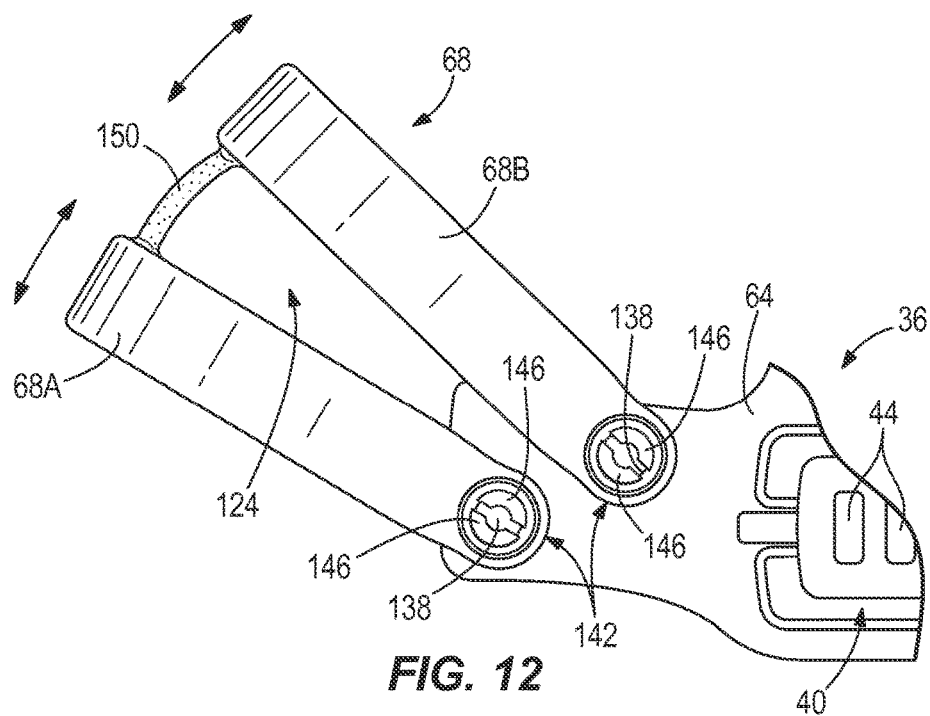
FIG. 12 is a side view of a portion of another example of a headgear capable of being used with the protective headwear shown in FIG. 1, according to one aspect of the present disclosure.

With reference to FIG. 12, another example of a forehead strap 68 is illustrated. One side of the forehead strap 68 and associated components are illustrated in FIG. 12, but it should be understood that the forehead strap 68 and associated components may be a substantial mirror image about a vertical plane extending through a center of the headgear (and a wearer's head when the headgear is worn). In other words, the forehead strap 68 and associated components may be symmetrical on both sides of a wearer's head as illustrated in FIG. 12. In this example, the forehead strap 68 is a pivoting forehead strap and pivots relative to the side members 64. Also, in this example, the forehead strap 68 is comprised of a first forehead strap 68A and a second forehead strap 68B. Both of the first and second forehead straps 68A, 68B are pivotally coupled to the side members 64 and are spaced-apart from one another. This example of the forehead strap 68 includes a space or cavity 124 between the first and second forehead straps 68A, 68B. Similar to the forehead strap 68 illustrated in FIGS. 2-4, each of the first and second forehead straps 68A, 68B define apertures 138 at their ends 142 that cooperate with pairs of projections 146 in order to couple and allow rotation of the first and second forehead straps 68A, 68B to the side members 64. The pairs of projections 146 and ends 142 of the forehead straps 68A, 68B may cooperate in similar manners to that described above in connection with the forehead strap 68 illustrated in FIGS. 2-4.

In this example, a support member 150 is coupled to and extends between the first and second forehead straps 68A, 68B. The support member 150 couples the first and second forehead straps 68A, 68B together and results in the first and second forehead straps 68A, 68B rotating together. Similar to other rotatable forehead straps of the present disclosure, the first and second forehead straps 68A, 68B are configured to accommodate various head sizes. The first and second foreheads straps 68A, 68B may rotate between any range of angles. In one example, since the first and second forehead straps 68A, 68B are coupled together by the support member 150, the first and second forehead straps 68A, 68B may rotate between the same angle. In the illustrated example, the headgear 36 associated with the first and second forehead straps 68A, 68B does not include any limiting members for engaging and limiting rotation of the first and second forehead straps 68A, 68B. In another example, the headgear 36 associated with the first and second forehead straps 68A, 68B may include a limiting member for each end 142 of both the first and second forehead straps 68A, 68B. In such an example, the headgear 36 would include four limiting members. In another example, the headgear 36 may include a limiting member for only one end 142 of each of the first and second forehead straps 68A, 68B. In such an example, the headgear 36 would include two limiting members. These two limiting members may be on complementary ends 142 of the first and second forehead straps 68A, 68B or opposite ends 142 of the first and second forehead straps 68A, 68B. In another example, only one of the first forehead strap 68A or second forehead strap 68B may have a limiting member(s) associated therewith. In such an example, the limiting member(s) may engage and limit only one of the first or second forehead straps 68A, 68B, but due to the coupling of the first and second forehead straps 68A, 68B together with the support member 150 the limiting member limits rotation of both the first and second forehead straps 68A, 68B. The illustrated example of the headgear 36 illustrates a single support member 150 between the first and second forehead straps 68A, 68B. In another example, the headgear 36 includes a plurality of support members 150 between the first and second forehead straps 68A, 68B. It should be understood that any number of support members may be coupled to and extend between the first and second forehead straps 68A, 68B and all of such possibilities are intended to be within the spirit and scope of the present disclosure.

Figure 13:
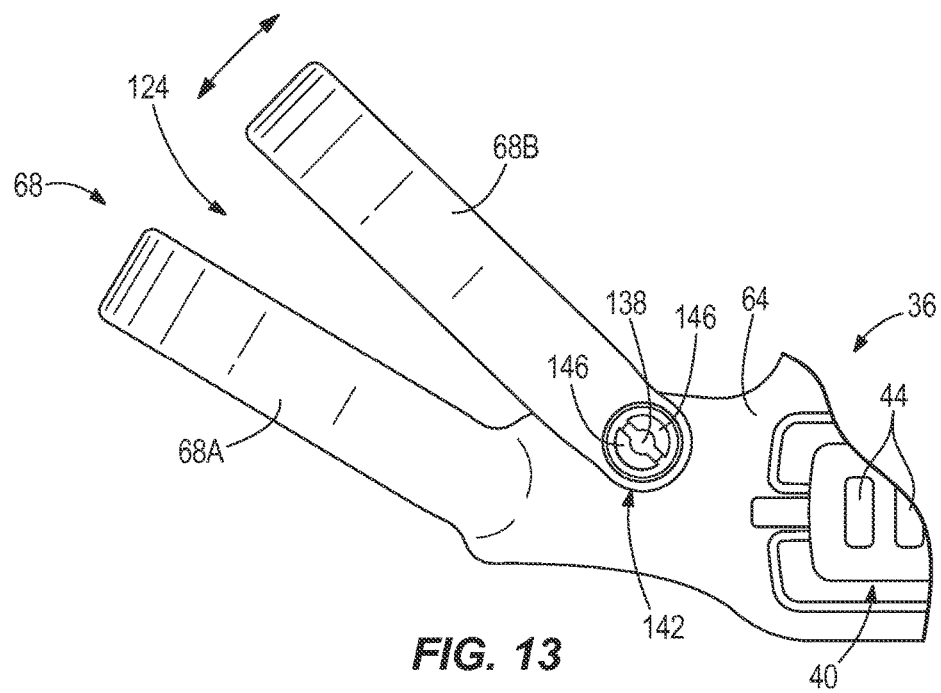
FIG. 13 is a side view of a portion of another example of a headgear capable of being used with the protective headwear shown in FIG. 1, according to one aspect of the present disclosure.

With reference to FIG. 13, another example of a forehead strap 68 is illustrated. One side of the forehead strap 68 and associated components are illustrated in FIG. 13, but it should be understood that the forehead strap 68 and associated components may be a substantial mirror image about a vertical plane extending through a center of the headgear (and a wearer's head when the headgear is worn). In other words, the forehead strap 68 and associated components may be symmetrical on both sides of a wearer's head as illustrated in FIG. 13. In this example, the forehead strap 68 is at least partially pivotal relative to the side members 64. Also, in this example, the forehead strap 68 is comprised of a first forehead strap 68A and a second forehead strap 68B. In this example, the first forehead strap 68A is rigidly coupled to and non-rotatable relative to the side members 64 and the second forehead strap 68B is pivotally coupled to the side members 64. The first and second forehead straps 68A, 68B are spaced-apart from one another to provide a space or cavity 124 there between. The space or cavity 124 changes in size as the second forehead strap 68B moves relative to the first forehead strap 68A. In the illustrated example, the first forehead strap 68A is unitarily formed as one-piece with the side members 64. In other examples, the first forehead strap 68A may be rigidly coupled to the side members 64 in a variety of manners including, but not limited to, bonding, adhering fastening, clipping, welding, fusing, or any other manner.

With continued reference to FIG. 13, and similar to the forehead strap 68 illustrated in FIGS. 2-4, the second forehead strap 68B defines apertures 138 at its ends 142 that cooperate with pairs of projections 146 in order to couple and allow rotation of the second forehead strap 68B to the side members 64. The pairs of projections 146 and ends 142 of the second forehead strap 68B may cooperate in similar manners to that described above in connection with the forehead strap 68 illustrated in FIGS. 2-4.

In this example, the second forehead strap 68B rotates relative to the first forehead strap 68A and the side members 64 to accommodate various head sizes. The second forehead strap 68B may rotate between any range or any angle. In the illustrated example, the headgear 36 associated with the first and second forehead straps 68A, 68B does not include any limiting member(s) for engaging and limiting rotation of the second forehead strap 68B. In another example, the headgear 36 associated with the first and second forehead straps 68A, 68B may include a limiting member for each end 142 of the second forehead strap 68B. In such an example, the headgear 36 would include two limiting members. In another example, the headgear 36 may include a limiting member for only one end 142 of the second forehead strap 68B. In such an example, the headgear 36 would include one limiting member.

Figure 14:
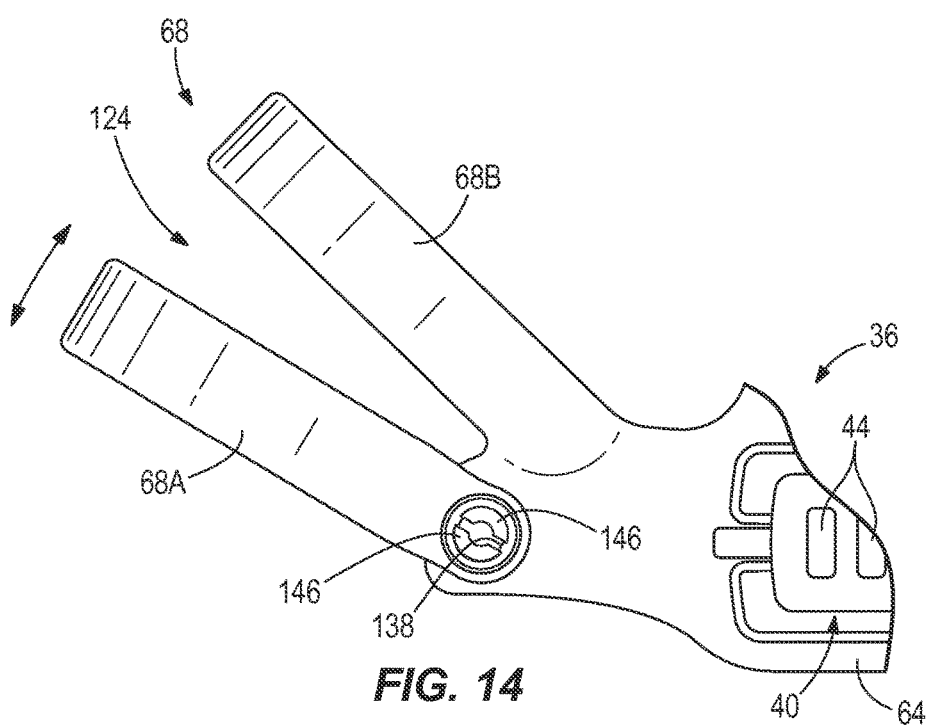
FIG. 14 is a side view of a portion of another example of a headgear capable of being used with the protective headwear shown in FIG. 1, according to one aspect of the present disclosure.

With reference to FIG. 14, another example of a forehead strap 68 is illustrated. One side of the forehead strap 68 and associated components are illustrated in FIG. 14, but it should be understood that the forehead strap 68 and associated components may be a substantial mirror image about a vertical plane extending through a center of the headgear (and a wearer's head when the headgear is worn). In other words, the forehead strap 68 and associated components may be symmetrical on both sides of a wearer's head as illustrated in FIG. 14. In this example, the forehead strap 68 is at least partially pivotal relative to the side members 64. Also, in this example, the forehead strap 68 is comprised of a first forehead strap 68A and a second forehead strap 68B. In this example, the second forehead strap 68B is rigidly coupled to and non-rotatable relative to the side members 64 and the first forehead strap 68A is pivotally coupled to the side members 64. The first and second forehead straps 68A, 68B are spaced-apart from one another to provide a space or cavity 124 there between. The space or cavity 124 changes in size as the first forehead strap 68A rotates relative to the second forehead strap 68B. In the illustrated example, the second forehead strap 68B is unitarily formed as one-piece with the side members 64. In other examples, the second forehead strap 68B may be rigidly coupled to the side members 64 in a variety of manners including, but not limited to, bonding, adhering fastening, clipping, welding, fusing, or any other manner.

With continued reference to FIG. 14, and similar to the forehead strap 68 illustrated in FIGS. 2-4, the first forehead strap 68A defines apertures 138 at its ends 142 that cooperate with pairs of projections 146 in order to couple and allow rotation of the first forehead strap 68A to the side members 64. The pairs of projections 146 and ends 142 of the first forehead strap 68A may cooperate in similar manners to that described above in connection with the forehead strap 68 illustrated in FIGS. 2-4.

In this example, the first forehead strap 68A rotates relative to the second forehead strap 68B and the side members 64 to accommodate various head sizes. The first forehead strap 68A may rotate between any range or any angle. In the illustrated example, the headgear 36 associated with the first and second forehead straps 68A, 68B does not include any limiting member(s) for engaging and limiting rotation of the first forehead strap 68A. In another example, the headgear 36 associated with the first and second forehead straps 68A, 68B may include a limiting member for each end 142 of the first forehead strap 68A. In such an example, the headgear 36 would include two limiting members. In another example, the headgear 36 may include a limiting member for only one end 142 of the first forehead strap 68A. In such an example, the headgear 36 would include one limiting member.

It should be understood that the headgear 36 may have a variety of shapes, sizes, and configurations and all of such possibilities are intended to be within the spirit and scope of the present disclosure.

It should be understood that the use of any orientation or directional terms herein such as, for example, "top", "bottom", "front", "rear", "back", "left", "right", "side", etc., is not intended to imply only a single orientation of the item with which it is associated or to limit the present disclosure in any manner. The use of such orientation or directional terms is intended to assist with the understanding of principles disclosed herein and to correspond to the exemplary orientation illustrated in the drawings. For example, the protective headwear 20 and headgear 36 may be utilized in any orientation and use of such terms is intended to correspond to the exemplary orientation of the protective headwear 20 and headgear 36 illustrated in the drawings. The use of these terms in association with the protective headwear 20 and headgear 36 is not intended to limit the protective headwear 20 and headgear 36 to a single orientation or to limit the protective headwear 20 and headgear 36 in any manner.

The Abstract of the disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

While various embodiments of the disclosure have been described, it will be apparent to those of ordinary skill in the art that other embodiments and implementations are possible within the scope of the disclosure. Accordingly, the disclosure is not to be restricted except in light of the attached claims and their equivalents.

The invention claimed is:

1. A headgear for engaging and supporting protective headwear on a wearer's head, the headgear comprising:
   a first side member on a first side of the headgear;
   a second side member on a second side of the headgear;
   a forehead strap pivotally coupled to and extending between the first and second side members, wherein the forehead strap includes an interior surface and padding positioned on the interior surface configured to engage a wearer's forehead with the headgear worn by a wearer;
   an occipital strap coupled to and extending between the first and second side members, wherein the occipital strap includes a pad coupled to the occipital strap and configured to engage a wearer's head with the headgear worn by a wearer;
   a top strap coupled to and extending between the first and second side members, wherein the top strap is coupled to the first and second side members between the forehead strap and the occipital strap, and wherein the top strap is configured to extend over a top of a wearer's head; and
   a rear strap coupled to and extending between the first and second side members, wherein the rear strap couples to the first and second side members between the top strap and the occipital strap;
   wherein the top strap is pivotally coupled to the first and second side members, and the rear strap is non-pivotally coupled to the first and second side members.

2. The headgear of claim 1, wherein the occipital strap is pivotally coupled to and extends between the first and second side members.

3. The headgear of claim 2, wherein the forehead strap rotates within a first range, wherein the first range of rotation of the forehead strap is between 1 degree and 90 degrees, and wherein the occipital strap rotates within a second range, wherein the second range of rotation of the occipital strap is between 1 degree and 90 degrees.

4. The headgear of claim 2, wherein the forehead strap rotates within a first range, wherein the first range of rotation of the forehead strap is between 5 degrees and 45 degrees, and wherein the occipital strap rotates within a second range, wherein the second range of rotation of the occipital strap is between 5 degrees and 45 degrees.

5. The headgear of claim 2, wherein the forehead strap rotates within a first range of 15 degrees, and wherein the occipital strap rotates within a second range of 15 degrees.

6. The headgear of claim 1, wherein the rear strap includes a first end and a second end, wherein the first end of the rear strap is of unitary construction with the first side member and the second end of the rear strap is of unitary construction with the second side member.

7. The headgear of claim 1, further comprising a limiting member engageable by the forehead strap to limit pivoting of the forehead strap.

8. The headgear of claim 7, wherein the limiting member extends from one of the first and second side members and is engageable by an edge of the forehead strap.

9. The headgear of claim 8, wherein the limiting member is engageable by a top edge and a bottom edge of the forehead strap to limit pivoting of the forehead strap in two directions.

10. A headgear for engaging and supporting protective headwear on a wearer's head, the headgear comprising:
 a first side member on a first side of the headgear;
 a second side member on a second side of the headgear;
 a forehead strap pivotally coupled to and extending between the first and second side members, wherein the forehead strap includes an interior surface and padding positioned on the interior surface configured to engage a wearer's forehead with the headgear worn by a wearer; and
 an occipital strap coupled to and extending between the first and second side members, wherein the occipital strap includes a pad coupled to the occipital strap and configured to engage a wearer's head with the headgear worn by a wearer;
 wherein the forehead strap is snap-fit connected to the first and second side members; and
 wherein an aperture is defined near each end of the forehead strap, wherein each of the first and second side members include a pair of resilient projections extending therefrom, and wherein the pair of resilient projections extending from the first side member insert into one of the apertures on one end of the forehead strap and the pair of resilient projections extending from the second side member insert into the other one of the apertures in the other end of the forehead strap.

11. A headgear for engaging and supporting protective headwear on a wearer's head, the headgear comprising:
 a first side member on a first side of the headgear, wherein the first side member includes a front end and a rear end;
 a second side member on a second side of the headgear, wherein the second side member includes a front end and a rear end;
 a forehead strap pivotally coupled to and extending between the front ends of the first and second side members, wherein the forehead strap is configured to engage a wearer's forehead with the headgear worn by a wearer;
 a rear strap coupled to and extending between the first and second side members, wherein the rear strap includes a first end non-rotatably coupled to the first side member and a second end non-rotatably coupled to the second side member; and
 a top strap configured to extend over a top of a wearer's head, wherein the top strap is coupled to and extends between the first and second side members, and wherein the top strap is coupled to the first and second side members between the forehead strap and the rear strap;
 wherein the forehead strap is snap-fit connected to the first and second side members;
 wherein an aperture is defined near each end of the forehead strap, wherein each of the first and second side members include a pair of resilient projections extending therefrom, and wherein the pair of resilient projections extending from the first side member insert into one of the apertures on one end of the forehead strap and the pair of resilient projections extending from the second side member insert into the other one of the apertures in the other end of the forehead strap.

12. The headgear of claim 11, wherein the forehead strap rotates within a range between 1 degree and 90 degrees.

13. The headgear of claim 11, wherein the forehead strap rotates within a range between 5 degrees and 45 degrees.

14. The headgear of claim 11, wherein the forehead strap rotates within a range of 15 degrees.

15. The headgear of claim 11, wherein the top strap is pivotally coupled to the first and second side members.

16. The headgear of claim 11, wherein the first end of the rear strap is of unitary construction with the first side member and the second end of the rear strap is of unitary construction with the second side member.

17. The headgear of claim 11, further comprising a limiting member engageable by the forehead strap to limit pivoting of the forehead strap.

18. The headgear of claim 17, wherein the limiting member extends from one of the first and second side members and is engageable by an edge of the forehead strap.

19. The headgear of claim 18, wherein the limiting member is engageable by a top edge and a bottom edge of the forehead strap to limit pivoting of the forehead strap in two directions.

* * * * *